United States Patent
Lee

(10) Patent No.: US 11,712,537 B2
(45) Date of Patent: Aug. 1, 2023

(54) PRESSURE SUPPORT, MECHANICAL INEXSUFFLATION, AND SUCTIONING SYSTEM AND METHOD

(71) Applicant: KONINKLIJKE PHILIPS N.V., Eindhoven (NL)

(72) Inventor: Seunghyun Lee, Valrico, FL (US)

(73) Assignee: Koninklijke Philips N.V., Eindhoven (NL)

( * ) Notice: Subject to any disclaimer, the term of this patent is extended or adjusted under 35 U.S.C. 154(b) by 342 days.

(21) Appl. No.: 16/722,585

(22) Filed: Dec. 20, 2019

(65) Prior Publication Data
US 2020/0197652 A1 Jun. 25, 2020

Related U.S. Application Data

(60) Provisional application No. 62/783,228, filed on Dec. 21, 2018.

(51) Int. Cl.
*A61M 16/00* (2006.01)
*A61M 16/20* (2006.01)
(Continued)

(52) U.S. Cl.
CPC ...... *A61M 16/202* (2014.02); *A61M 16/0009* (2014.02); *A61M 16/0463* (2013.01);
(Continued)

(58) Field of Classification Search
CPC .............. A61M 16/00; A61M 16/0463; A61M 16/202; A61M 16/0009; A61M 16/201;
(Continued)

(56) References Cited

U.S. PATENT DOCUMENTS 6,886,561 B2 * 5/2005 Bayron ............... F16K 11/0716
128/207.14
9,795,752 B2 * 10/2017 Birnkrant .......... A61M 16/0006
(Continued)

FOREIGN PATENT DOCUMENTS

| EP | 2367586 A2 | 9/2011 |
| WO | 2007/054829 A2 | 5/2007 |
| WO | WO-2018106808 A1 * | 6/2018 ........ A61M 16/0463 |

OTHER PUBLICATIONS

Christopher J Russian, Respiratory Care, 2014. "Suction Catheter Size: An Assessment and Comparison of 3 Different Calculation Methods", 59 (1) 32-38). (Year: 2014) (Year: 2014).*
(Continued)

*Primary Examiner* — Philip R Wiest
*Assistant Examiner* — Sarah B Lederer
(74) *Attorney, Agent, or Firm* — Daniel H. Brean; Andrew M. Gabriel

(57) ABSTRACT

The present disclosure pertains to a system and method for facilitating pressure support therapy, mechanical inexsufflation therapy, and suctioning therapy for a subject. The system and method described herein offer a novel combination of mechanical inexsufflation with suctioning from a vacuum system. The invasive nature of current closed suctioning systems poses many potential risks, such as tissue trauma, less optimum secretion clearance at the peripheral airway, and lung decruitment. The system and method described herein provide a non-invasive method of suctioning with a suctioning volume measurement and a monitoring alarm to ensure a baseline lung volume and a positive end expiratory pressure (PEEP) level are maintained. This non-invasive method of suctioning is provided together with mechanical inexsufflation and pressure support therapy.

19 Claims, 4 Drawing Sheets

(51) Int. Cl.
*A61M 16/04* (2006.01)
*A61M 16/08* (2006.01)

(52) U.S. Cl.
CPC ..... *A61M 16/0066* (2013.01); *A61M 16/0075* (2013.01); *A61M 16/0833* (2014.02); *A61M 16/203* (2014.02); *A61M 2205/502* (2013.01)

(58) Field of Classification Search
CPC .............. A61M 16/205; A61M 16/204; A61M 16/0003; A61M 16/161
See application file for complete search history.

(56) References Cited

U.S. PATENT DOCUMENTS

| | | | | |
|---|---|---|---|---|
| 9,956,371 | B2* | 5/2018 | DeVries | A61M 16/0808 |
| 2007/0017523 | A1 | 1/2007 | Be-Eri | |
| 2007/0199566 | A1 | 8/2007 | Be'Eri | |
| 2012/0199127 | A1* | 8/2012 | Garde | A61M 16/024 |
| | | | | 128/204.23 |
| 2014/0121607 | A1* | 5/2014 | Chang | A61M 16/0833 |
| | | | | 604/246 |
| 2015/0027444 | A1* | 1/2015 | Col, Jr. | A61M 16/0009 |
| | | | | 128/204.21 |
| 2016/0279375 | A1 | 9/2016 | Devries et al. | |
| 2017/0173283 | A1* | 6/2017 | Li | A61M 16/206 |
| 2017/0333653 | A1* | 11/2017 | Lee | A61M 16/026 |

OTHER PUBLICATIONS

Christopher J Russian, Respiratory Care, 2014. "Suction Catheter Size: An Assessment and Comparison of 3 Different Calculation Methods", 59 (1) 32-38). (Year: 2014).*

International Search Report and Written Opinion dated Mar. 31, 2020 for International Application No. PCT/EP2019/086189 Filed Dec. 19, 2019.

* cited by examiner

PRESSURE SUPPORT, MECHANICAL INEXSUFFLATION, AND SUCTIONING SYSTEM AND METHOD

CROSS-REFERENCE TO PRIOR APPLICATIONS

This application claims the benefit of U.S. Provisional Application No. 62/783,228, filed on 21 Dec. 2018. This application is hereby incorporated by reference herein.

BACKGROUND

1. Field

The present disclosure pertains to a system and method for facilitating pressure support therapy, mechanical inexsufflation therapy, and suctioning therapy for a subject.

2. Description of the Related Art

Pressure support systems, mechanical inexsufflation systems, and suctioning therapy systems are known. For example, intubated patients in intensive care units (ICUs) do not produce an effective cough to clear airway secretions. Endotracheal suctioning is performed to remove pulmonary secretions from a patient's airway. Inadequate removal of pulmonary secretions may result in various clinical complications, including atelectasis, pneumonia, or respiratory failure. Clinicians routinely perform endotracheal suctioning on the patients in ICU to prevent these complications. However, to perform this procedure, a clinician typically needs to disconnect, connect, or rearrange various portions of a breathing circuit coupled to a patient's airway to change from pressure support or mechanical inexsufflation therapy and facilitate suctioning.

SUMMARY

It would be advantageous to provide a system and method for facilitating pressure support therapy, mechanical inexsufflation therapy, and suctioning therapy for a subject.

Accordingly, one or more aspects of the present disclosure relate to a system configured to facilitate pressure support therapy, mechanical inexsufflation therapy, and suctioning therapy for a subject. The system comprises a flow manifold configured to communicate with a pressure support system, a mechanical inexsufflation system, a vacuum system, and a respiratory circuit. The respiratory circuit is in communication with an airway of the subject. The flow manifold comprises a plurality of ports configured to removably couple with the pressure support system, the mechanical inexsufflation system, the vacuum system, and the respiratory circuit. The flow manifold comprises a flow channel configured to place the respiratory circuit in fluid communication with the pressure support system, the mechanical inexsufflation system, and the vacuum system by connecting the plurality of ports to each other. The system comprises a valve configured to operate in a first mode to facilitate gas flow between the respiratory circuit and the pressure support system to provide the pressure support therapy to the subject; and a second mode to facilitate gas flow between the respiratory circuit, the mechanical inexsufflation system, and the vacuum system to provide the mechanical inexsufflation therapy and the suctioning therapy to the subject.

In some embodiments, the flow channel is closed to ambient atmosphere when the valve operates in the first mode and the second mode.

In some embodiments, the plurality of ports comprises: a first port configured to couple with the pressure support system; a second port configured to couple with the mechanical inexsufflation system; a third port configured to couple with the vacuum system; and a fourth port configured to couple with the respiratory circuit. The valve is configured to facilitate gas flow between the fourth port and the first port in the first mode; and facilitate gas flow between the fourth port, the third port, and the second port in the second mode.

In some embodiments, the third port is configured to receive a suctioning catheter of the vacuum system. The third port, the valve, and the flow channel are configured to facilitate advancement of the suctioning catheter through the flow channel and the fourth port into an endotracheal tube of the respiratory circuit.

In some embodiments, the system comprises or more sensors configured to generate output signals conveying information related to gas flow through the flow manifold; and one or more processors in operative communication with the one or more sensors, the pressure support system, the mechanical inexsufflation system, and/or the vacuum system. The one or more processors are configured by computer readable instructions to: control the pressure support system to provide the pressure support therapy to the subject based on the information in the output signals; control, based on the information in the output signals, the mechanical inexsufflation system to provide the mechanical inexsufflation therapy to the subject such that a volume of gas exsufflated from the airway of the subject during an exsufflation phase of the mechanical inexsufflation therapy is equal to a volume of gas insufflated by the subject during a corresponding insufflation phase; and/or determine, based on the information in the output signals, a suctioning volume of gas suctioned by the vacuum system, and, responsive to the suctioning volume of gas breaching a suctioning volume threshold, controlling the valve to change from operating in the second mode to operate in the first mode.

In some embodiments, the system comprises the pressure support system, the inexsufflation system, and the vacuum system. In some embodiments, the one or more sensors comprise a pneumotachometer.

In some embodiments, the one or more processors are configured to determine the suctioning volume threshold based on a suctioning catheter diameter, an endotracheal tube diameter, and the volume of gas exsufflated from the airway of the subject during the exsufflation phase of the mechanical inexsufflation therapy.

In some embodiments, the valve is configured to be manually changed between operating in the first mode and operating in the second mode.

In some embodiments, the flow manifold comprises a housing configured to hold the flow channel and the valve.

Another aspect of the present disclosure relates to a method for facilitating pressure support therapy, mechanical inexsufflation therapy, and suctioning therapy for a subject with a therapy system. The system comprises a flow manifold and a valve. The method comprises facilitating, with the flow manifold, communication between a pressure support system, a mechanical inexsufflation system, a vacuum system, and a respiratory circuit. The respiratory circuit is in communication with an airway of the subject. The flow manifold comprises a plurality of ports configured to removably couple with the pressure support system, the mechanical inexsufflation system, the vacuum system, and the respiratory circuit; and a flow channel configured to place the respiratory circuit in fluid communication with the pressure support system, the mechanical inexsufflation system, and the vacuum system by connecting the plurality of ports to each other. The method comprises facilitating, with the valve operating in a first mode, gas flow between the respiratory circuit and the pressure support system to provide the pressure support therapy to the subject; and facilitating, with the valve operating in a second mode, gas flow between the respiratory circuit, the mechanical inexsufflation system, and the vacuum system to provide the mechanical inexsufflation therapy and the suctioning therapy to the subject.

In some embodiments, the flow channel is closed to ambient atmosphere when the valve operates in the first mode and the second mode.

In some embodiments, the method further comprises generating, with one or more sensors of the system, output signals conveying information related to gas flow through the flow manifold; controlling, with one or more processors of the system, the pressure support system to provide the pressure support therapy to the subject based on the information in the output signals; controlling, with the one or more processors, based on the information in the output signals, the mechanical inexsufflation system to provide the mechanical inexsufflation therapy to the subject such that a volume of gas exsufflated from the airway of the subject during an exsufflation phase of the mechanical inexsufflation therapy is equal to a volume of gas insufflated by the subject during a corresponding insufflation phase; and/or determining, with the one or more processors, based on the information in the output signals, a suctioning volume of gas suctioned by the vacuum system, and, responsive to the suctioning volume of gas breaching a suctioning volume threshold, controlling the valve to change from operating in the second mode to operate in the first mode.

In some embodiments, the method further comprises determining, with the one or more processors, the suctioning volume threshold based on a suctioning catheter diameter, an endotracheal tube diameter, and the volume of gas exsufflated from the airway of the subject during the exsufflation phase of the mechanical inexsufflation therapy.

In some embodiments, the method further comprises facilitating manually changing the valve between operating in the first mode and operating in the second mode.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
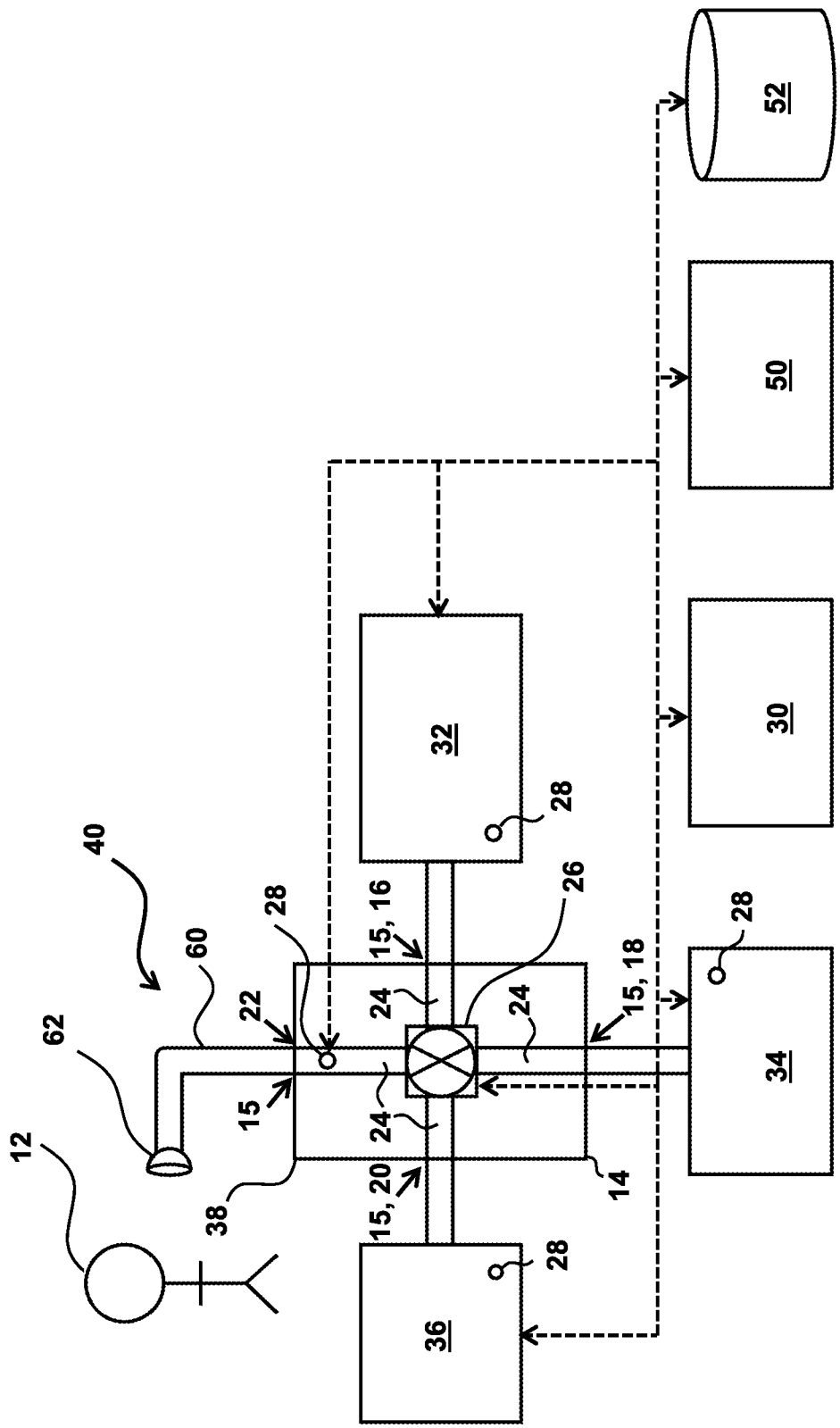
FIG. 1 schematically illustrates a system configured to facilitate pressure support therapy, mechanical inexsufflation therapy, and suctioning therapy for a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a system 10 configured to facilitate pressure support therapy, mechanical inexsufflation therapy, and suctioning therapy for a subject 12. Typical endotracheal suctioning presents clinical hazards and complications such as lung de-recruitment and loss of positive end expiratory pressure (PEEP), atelectasis, tissue trauma to the tracheal and/or bronchial mucosa, bronchoconstriction/bronchospasm, increased microbial colonization of the lower airway, cardiac dysrhythmias, and patient discomfort. A typical closed endotracheal suctioning, also known as in-line suctioning, system connects to a "Y" adaptor on a ventilator respiratory circuit at or near an endotracheal tube. A suction catheter of the suctioning system is connected to a canister, which is connected to a pressure regulated vacuum source. The suction catheter is advanced through the endotracheal tube until resistance is met. A patient's carina is stimulated, inducing a strong cough reflex. Then, suction is applied as the suction catheter is being withdrawn from the endotracheal tube.

The invasive nature of typical endotracheal suctioning often leads to tissue trauma to the tracheal and bronchial mucosa, bronchoconstriction/bronchospasm, cardiac dysrhythmias, and patient discomfort. Typical endotracheal suctioning is a direct contact suction at the main bronchus level and does not effectively clear secretions in a patient's lower airway. In addition, over suctioning may result in lung de-recruitment and/or loss of PEEP. Under suctioning may lead to inadequate clearance of pulmonary secretions, a mucus plug, and/or eventually to atelectasis.

Mechanical inexsufflation (M I-E) is a non-invasive method of secretion clearance. However, mechanical inexsufflation requires breaking a pressure support (e.g., ventilator) respiratory circuit to couple the mechanical inexsufflation system to a patient's airway. This results in an increased risk of contamination and infection. In addition, some form of direct suctioning is still needed, even with or after mechanical inexsufflation, to remove secretions from the endotracheal tube. Thus, typical mechanical inexsufflation may address hazards associated with invasive endotracheal suctioning, but presents similar complications related to lung de-recruitment and loss of PEEP.

System 10 facilitates a novel integrated combination of mechanical inexsufflation and in-line closed suctioning, with pressure support therapy. Among other advantages, system 10 is configured such that mechanical inexsufflation provides hyperinflation of the lungs of subject 12 with a targeted lung volume. The hyperinflation allows air to pass behind the mucus on the bronchial wall or alveolus through various collateral channels. Adequately inflated lungs promote more effective expulsion of secretions as the air behind the mucus mobilizes toward an endotracheal tube. Conventional suctioning, for example, does not provide the hyperinflation of the lung before suctioning. Instead, conventional suctioning hypoinflates the lungs because of the partial obstruction of the endotracheal lumen as a suction catheter advances through the endotracheal tube.

In system 10, the exsufflation phase of mechanical inexsufflation delivers non-invasive suctioning, overcoming the common clinical risks and hazards associated with the invasive closed suction method described above. In system 10, the same volume of gas delivered during the hyperinflation phase (e.g., insufflation) of mechanical inexsufflation is also removed during the corresponding exsufflation phase. This volume controlled suctioning mechanism assures the recruitment of subject 12's lung volume, while maintaining a prescribed PEEP level.

In addition, system 10 is configured such that a shorter (compared to typical systems) version of a closed suctioning catheter may be advanced into an endotracheal tube to remove mobilized secretions during mechanical inexsufflation. System 10 is configured to facilitate suctioning and mechanical inexsufflation therapy without breaking a pressure support system (e.g., ventilator) respiratory circuit. System 10 is configured to monitor a total suctioning volume and change an operational mode of system 10 back to pressure support, or prompt a clinician visually or audibly to change the operational mode, responsive to a breach of a total suctioning volume threshold.

In some embodiments, system 10 comprises one or more of a flow manifold 14 with a valve 26, a pressure support system 32, a mechanical inexsufflation system 34, a vacuum system 36, a respiratory circuit 40, one or more sensors 28, a processor 30, a user interface 50, electronic storage 52, and/or other components.

Flow manifold 14 is configured to communicate with pressure support system 32, mechanical inexsufflation system 34, vacuum system 36, respiratory circuit 40, and/or other components of system 10. Respiratory circuit 40 is in communication with the airway of subject 12 as described below. The flow manifold comprises a plurality of ports 15, a flow channel 24, and/or other components. In some embodiments, flow manifold 14 comprises a housing 38 configured to hold flow channel 24, valve 26, and/or other components of system 10. In some embodiments, ports 15 are formed in and/or by housing 38. In some embodiments, ports 15 are configured to facilitate removable coupling of various components of system 10 with flow manifold 14.

Ports 15 are configured to removably couple with pressure support system 32, mechanical inexsufflation system 34, vacuum system 36, and respiratory circuit. In some embodiments, coupling may comprise a removable attachment. In some embodiments, coupling may be accomplished through added plumbing and/or additional manufactured parts configured to couple the components described herein. Ports 15 comprise a first port 16 configured to couple with pressure support system 32. Ports 15 comprise a second port 18 configured to couple with mechanical inexsufflation system 34. Ports 15 comprise a third port 20 configured to couple with vacuum system 36. Ports 15 comprise a fourth port 22 configured to couple with respiratory circuit 40.

Flow channel 24 is configured to place respiratory circuit 40 in fluid communication with pressure support system 32, mechanical inexsufflation system 34, and vacuum system 36 by connecting the plurality of ports 15 to each other. In some embodiments, flow channel 24 comprises one or more hollow areas within flow manifold 14. In some embodiments, one or more portions of flow channel 24 may have a columnar shape with a generally cylindrical cross section. In some embodiments, a diameter of the cylindrical cross section may vary within flow manifold 14.

Valve 26 is configured to selectively control gas flow through flow manifold 14 and flow channel 24. Valve 26 is positioned along flow channel 24 between first port 16, second port 18, third port 20, and fourth port 22. Valve 26 is configured to guide gas flow through one or more portions of flow channel 24. Valve 26 is configured to operate in a first mode to facilitate gas flow between respiratory circuit 40 and pressure support system 32 to provide the pressure support therapy to subject 12. Valve 26 is configured to operate in a second mode to facilitate gas flow between respiratory circuit 40, mechanical inexsufflation system 34, and vacuum system 36 to provide the mechanical inexsufflation therapy and the suctioning therapy to subject 12. Valve 26 is configured to facilitate gas flow between fourth port 22 and first port 16 in the first mode; and facilitate gas flow between fourth port 22, third port 20, and second port 18 in the second mode.

Valve 26 may be configured to be automatically (e.g., by processor 30) or manually (e.g., by subject 12 and/or another user) changed between operating in the first mode and operating in the second mode. In some embodiments, valve 26 may comprise one or more valves in series and/or in parallel. Examples of valves and/or other pressure regulating devices suitable for use as valve 26 comprise, a plug valve, a ball valve, a check valve, a butterfly valve, a solenoid, and/or other pressure regulating devices. The pressure regulating devices mentioned above and/or other pressure regulating devices that may be used as valve 26 may be controlled manually, mechanically, magnetically, hydraulically, pneumatically, electronically (e.g., via an electric motor), and/or another mode of control configured to open and/or close a valve and/or other pressure control device.

Figure 2:
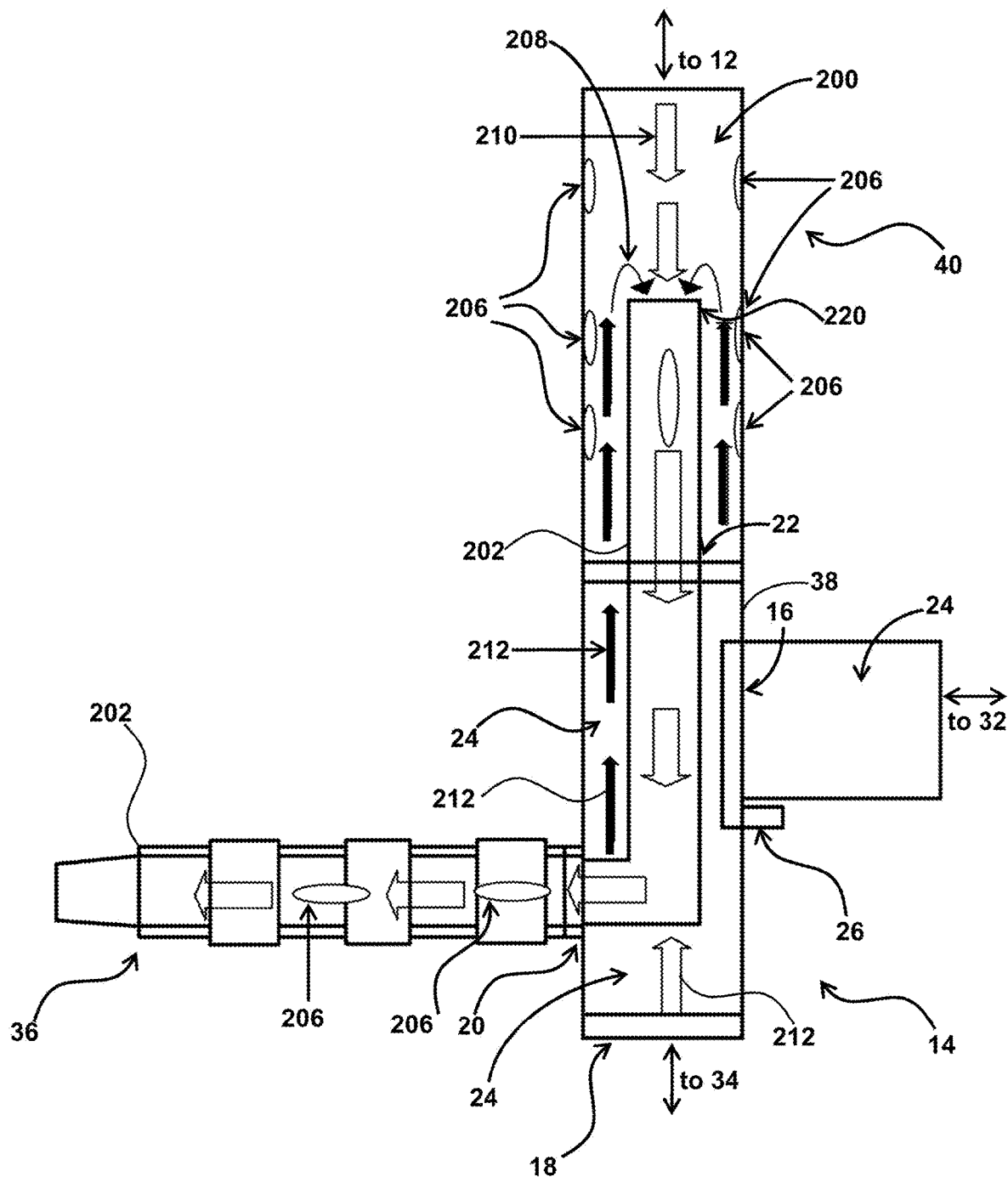
FIG. 2 illustrates a flow manifold of the present system.

By way of a non-limiting example, FIG. 2 illustrates flow manifold 14. FIG. 2 illustrates a more detailed version of flow manifold 14 compared to the version shown in FIG. 1. FIG. 2 illustrates flow manifold 14 with valve 26 operating in the second mode to facilitate gas flow between respiratory circuit 40, mechanical inexsufflation system 34, and vacuum system 36 to provide the mechanical inexsufflation therapy and the suctioning therapy to subject 12. As shown in FIG. 2, valve 26 is configured to facilitate gas flow between fourth port 22 and third port 20, and second port 18 in the second mode. In FIG. 2, respiratory circuit 40 includes an endotracheal tube 200 and/or other components. A suctioning catheter 202 of vacuum system 36 is also shown in FIG. 2.

In the example shown in FIG. 2, suctioning catheter 202 has been received by flow manifold 14 at third port 20 and has been advanced through flow channel 24 into endotracheal tube 200. Third port 20, valve 26, and flow channel 24 are configured (via various components, fittings, a port shape, a catheter shape, etc.) to facilitate advancement of suctioning catheter 202 through flow channel 24 and fourth port 22 into an endotracheal tube (e.g., a conduit and/or interface appliance as described below) of respiratory circuit 40. As shown in FIG. 2, flow channel 24 is closed to ambient atmosphere (e.g., there are no openings to the outside atmosphere) when valve 26 operates in the second mode. It should be noted that flow channel 24 is also closed to ambient atmosphere when valve 26 operates in the first mode (e.g., as shown in FIG. 3 described below).

FIG. 2 illustrates mucus 206 being suctioned into 208 catheter 202. Mucus 206 is suctioned from two different directions. Mucus is suctioned from respiratory circuit 40 and subject 12 in a first (e.g., which may be termed "upward") suctioning direction 210 and from mechanical inexsufflation system 34 in a second (e.g., which may be termed "downward") direction 212. The suctioning 210 is augmented by the suctioning 212 pathway from mechanical inexsufflation system 34 to the tip 220 of suctioning catheter 202 as shown in FIG. 2. The downward suctioning pathway enables the suctioning flow to sweep the mobilized mucus from an M I-E cycle from the tip of an endotracheal tube (e.g., that is part of respiratory circuit 40) to the tip of suctioning catheter 202 in a gravitational direction, further enhancing secretion removal.

Figure 3:
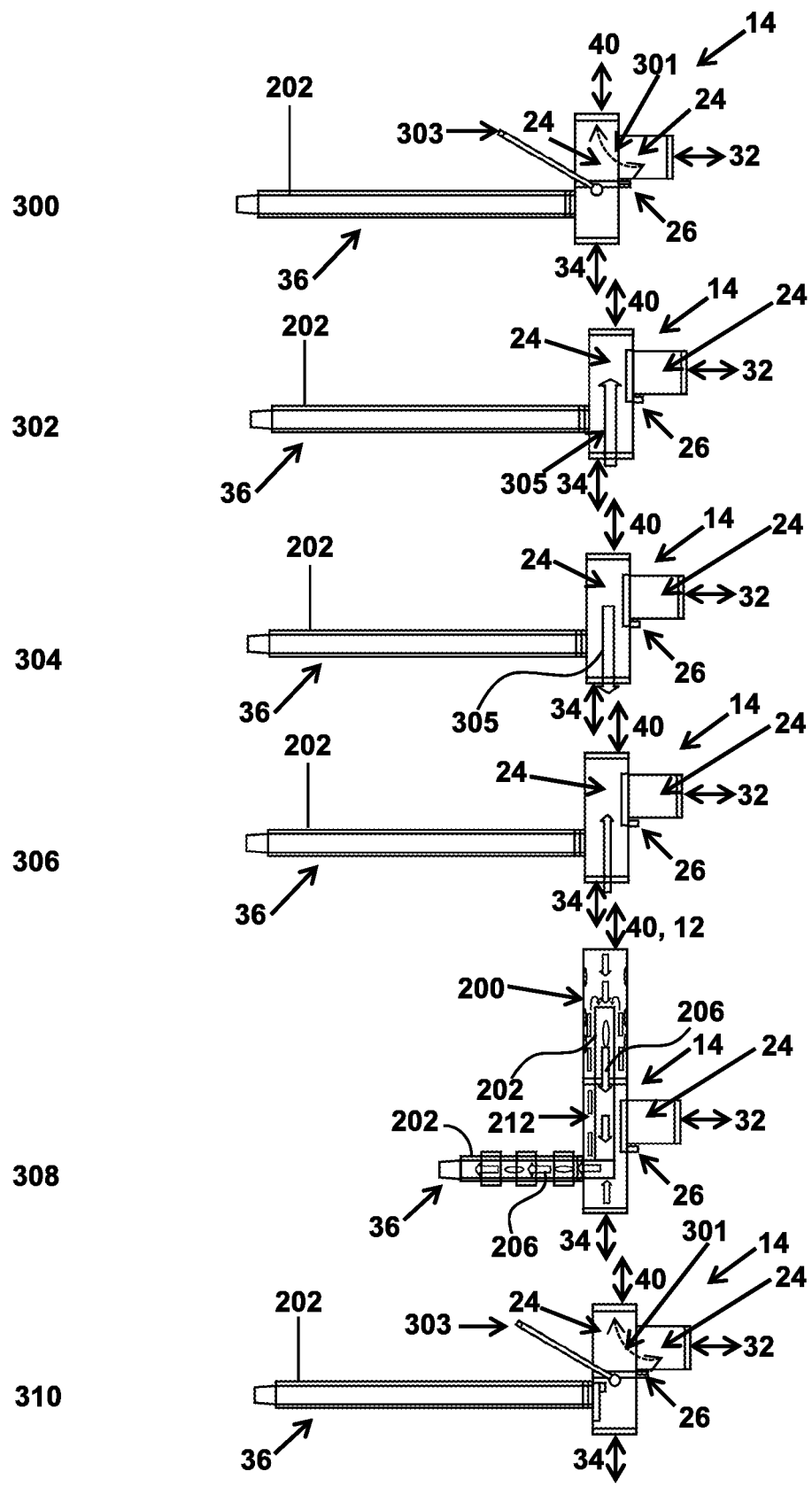
FIG. 3 illustrates several views of the flow manifold and a valve of the present system in configurations that facilitate provision of pressure support therapy, mechanical inexsufflation therapy, and suctioning therapy to the subject.

By way of a second non-limiting example, FIG. 3 illustrates several views 300, 302, 304, 306, 308, and 310 of flow manifold 14 and valve 26 in configurations that facilitate provision of pressure support therapy, mechanical inexsufflation therapy, and suctioning therapy to subject 12 (FIG. 1). View 300 illustrates valve 26 operating in the first mode, configured to facilitate airflow 301 between pressure support system 32 and respiratory circuit 40. Flow manifold 14 and valve 26 may facilitate ventilation in the configuration shown in view 300, for example. View 300 also illustrates an optional flush port 303 configured to vent gases from flow channel 24 to ambient atmosphere if controlled by a user to do so.

Views 302 and 304 illustrate valve 26 operating in the second mode (valve 26 has changed position) facilitating flow between mechanical inexsufflation system 34 and respiratory circuit 40. Specifically, view 302 illustrates flow manifold 14 and valve 26 during an insufflation phase of mechanical inexsufflation therapy provided to subject 12 (FIG. 1). View 302 shows airflow 305 flowing toward respiratory circuit 40, for example. View 304 illustrates flow manifold 14 and valve 26 during an exsufflation phase of mechanical inexsufflation therapy provided to subject 12 (FIG. 1). View 304 shows airflow 305 flowing toward mechanical inexsufflation system 34, for example. View 306 illustrates a pause phase where air is not flowing in either direction.

View 308 illustrates valve 26 continuing to operate in the second mode while suctioning therapy is provided to subject 12 (FIG. 1). View 308 is a reproduction of FIG. 2 and illustrates suctioning catheter inserted into flow channel 24 and endotracheal tube 200.

View 310 re-illustrates valve 26 back operating in the first mode, configured to facilitate airflow 301 between pressure support system 32 and respiratory circuit 40. Flow manifold 14 and valve 26 may again facilitate ventilation in the configuration shown in view 310, for example. The view progression shown in FIG. 3 (views 300-310) illustrates how flow manifold 14 and valve 26 facilitate integration of the "y" connection from a mechanical ventilator (e.g., a pressure support system 32), a closed suctioning port (e.g., port 20 configured to receive suctioning catheter 202), and a mechanical inexsufflation system (e.g., mechanical inexsufflation system 34).

Returning to FIG. 1, pressure support system 32 is configured to provide a pressurized flow of breathable gas for delivery to the airway of subject 12. In some embodiments, pressure support therapy system 32 is configured to generate the flow of gas in accordance with a positive pressure support therapy regime. In positive airway pressure support therapy, the pressurized flow of gas generated by pressure support system 32 is controlled to replace and/or compliment subject 12's regular breathing. Positive airway pressure support therapy may be used to maintain an open airway in subject 12 so that oxygen and carbon dioxide may be exchanged more easily, requiring little and/or no effort from subject 12. By way of non-limiting example, pressure support system 32 may be configured such that the pressure support provided to subject 12 via the pressurized flow of breathable gas comprises ventilation therapy, continuous positive airway pressure support (CPAP), bi-level positive airway pressure support (BPAP), proportional positive airway pressure support (PPAP), and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) to promote or assist tidal ventilation. In some therapy modes (e.g., PPAP), variable pressure support, in which the amount of pressure delivered to the patient during inhalation and/or during exhalation is determined and delivered on a breath by breath basis, may be applied. In some embodiments, pressure support therapy system 32 may be configured to temporarily drop the supplied pressure during exhalation (C-Flex, Airway Pressure Release Ventilation (APRV)) to reduce exhalation effort required by subject 12.

In some embodiments, pressure support system 32 may be configured to deliver staged pressure support therapy. In staged pressure support therapy, the pressure delivered gradually increases over time. In some embodiments, pressure support system 32 may switch therapy modes based on information related to the respiration of subject 12 and/or other information. For example, pressure support therapy system 32 may change from BPAP to CPAP after a certain number of breaths by subject 12 and/or by some external monitor, caregiver and/or alert, such as in rescue and/or apnea ventilation.

Pressure support system 32 receives a flow of gas from a gas source, such as the ambient atmosphere, and elevates the pressure of that gas for delivery to the airway of subject 12. Pressure support system 32 may include any device, such as, for example, a pump, blower, piston, or bellows, that is capable of elevating the pressure of the received gas for delivery to subject 12. The present disclosure also contemplates that gas other than ambient atmospheric air may be introduced into system 10 for delivery to subject 12. In such embodiments, a pressurized canister or tank of gas containing air, oxygen, and/or another gas may supply the intake of pressure support system 32.

Pressure support system 32 may comprise one or more valves for controlling the pressure and/or flow direction of gas, a manifold defining the gas flow path in pressure support system 32, conduits and/or hoses configured to couple with flow manifold 14, and/or other components. The present disclosure also contemplates controlling the operating speed of a blower of pressure support system 32, for example, either alone or in combination with such valves and/or the manifold, to control the pressure/flow of gas provided to subject 12.

Mechanical inexsufflation system 34 is configured to provide a pressurized flow of breathable gas for delivery to the airway of subject 12 (inflow to subject 12) and/or to draw gas from the airway (outflow from subject 12) of subject 12 (e.g., to inexsufflate). Mechanical inexsufflation system 34 may be configured such that one or more gas parameters of the pressurized flow of breathable gas are controlled in accordance with an inexsufflation therapy regime to inexsufflate subject 12. The one or more gas parameters may include, for example, one or more of volume, pressure, flow rate, time, humidity, velocity, acceleration, and/or other parameters. Like pressure support system 32, mechanical inexsufflation system 34 receives a flow of gas from a gas source and elevates the pressure of that gas for delivery to the airway of subject 12. Mechanical inexsufflation system 34 may comprise one or more valves for controlling the pressure and/or flow direction of gas in system 34, a manifold defining the gas flow path in system 34, and/or other components.

By way of a non-limiting example, mechanical inexsufflation system 34 may be configured to adjust the parameters of the pressurized flow of breathable gas in accordance with an inexsufflation therapy regime. In one embodiment, the therapy regime may dictate that the pressurized flow of breathable gas is delivered to the airway of subject 12 at a first pressure and time corresponding to a target volume during insufflation. This volume is sufficiently high enough that the lung volume of subject 12 is at least partially recruited during insufflation. After insufflation, mechanical inexsufflation system 34 may reduce the pressure of the pressurized flow of breathable gas with sufficient abruptness that expiratory flow through the airway of subject 12 is sufficient to remove mucus and/or other debris from the airway and/or lungs of subject 12. The pressure may be reduced from the first pressure level to a second pressure level that is substantially lower than the first pressure level. The second pressure level may, for example, be a negative pressure, below atmospheric pressure. After expiration is complete, pressure generator 14 may return the pressure of the pressurized flow of breathable gas to the first pressure level to facilitate another inspiration in preparation for another inexsufflation. After a series of inexsufflations, inexsufflation may be ceased.

Vacuum system 36 is configured to provide suctioning therapy to subject 12. Vacuum system 36 is configured to create a negative pressure that is applied to the airway of subject 12, flow channel 24, and/or other components. Vacuum system 36 is configured to suck and/or otherwise remove secretions (e.g., flem, mucus, etc.) from the airway of subject 12, flow channel 24 and/or other locations. Vacuum system 36 may include a vacuum pump (e.g., including a motor) and/or other vacuum sources, a catheter, and/or other components (e.g., as described herein). In some embodiments, the vacuum pump draws a vacuum that is applied to the catheter at or near a proximal end of the catheter. In some embodiments, the vacuum pump is coupled to the catheter via flexible tubing and/or other components, for example. Vacuum system 36 is configured such that a distal end of the catheter (e.g., an end opposite the connection to the vacuum pump) is configured to be inserted into flow manifold 14 at or near port 20. The catheter may be advanced into and through flow manifold 14 and flow channel 24, for example (e.g., as shown in FIGS. 2 and 3). In some embodiments, vacuum system includes a thumb (for example) plunger control configured to allow a user to selectively apply the vacuum from the vacuum pump to the catheter. For example, a user may depress the plunger when the user wants the vacuum to be applied to the catheter, and release the plunger when the user wants the vacuum to cease. This example is not intended to be limiting. Other vacuum control mechanisms are contemplated.

Respiratory circuit 40 is configured to deliver the positive pressure therapy (e.g., the pressurized flow of breathable gas), the mechanical inexsufflation therapy, the suctioning therapy, and/or therapies to the airway of subject 12. As such, respiratory circuit comprises a conduit 60, an interface appliance 62, and/or other components. Conduit 60 is configured to convey gas to and from (e.g., gas from subject 12 may include mucus, etc.) interface appliance 62 and/or the airway of subject 12. Conduit 60 may be a flexible length of hose, or other conduit, that places interface appliance 62 in fluid communication with flow manifold 14. Interface appliance 62 is configured to deliver gas to, and receive gas (and/or mucus, etc.) from, the airway of subject 12. In some embodiments, interface appliance 62 is configured to be removably coupled with conduit 60 and/or other conduits and/or interface appliances being used to deliver therapy to subject 12. In some embodiments, interface appliance 62 is non-invasive. As such, interface appliance 62 non-invasively engages subject 12.

Non-invasive engagement comprises removably engaging an area (or areas) surrounding one or more external orifices of the airway of subject 12 (e.g., nostrils and/or mouth) to communicate gas between the airway of subject 12 and interface appliance 62. Some examples of non-invasive interface appliance 62 may comprise, for example, a nasal cannula, a nasal mask, a nasal/oral mask, a full-face mask, a total face mask, or other interface appliances that communicate a flow of gas with an airway of a subject. In some embodiments, interface appliance 62 is invasive. Some examples of invasive interface appliances that may comprise interface appliance 62 are endotracheal tubes, tracheostomy tubes, and or other devices. The present disclosure is not limited to these examples, and contemplates delivery of the flow of gas to the subject using any interface appliance.

Although respiratory circuit 40 is illustrated in FIG. 1 as a single-limbed interface for the delivery of gas to the airway of subject 12, this is not intended to be limiting. The scope of this disclosure comprises double-limbed circuits having a first limb configured to both provide the flow of gas to the airway of the subject, and a second limb configured to selectively exhaust gas (e.g., to exhaust exhaled gases).

Sensor(s) 28 are configured to generate output signals conveying information related to gas flow through flow manifold 14 and/or other components of system 10. In some embodiments, sensor(s) 28 are configured to generate output signals conveying information related to one or more parameters of the flow of gas. The parameters may include parameters related to gas within respiratory circuit 40, gas within flow manifold 14, gas within pressure support system 32, gas within mechanical inexsufflation system 34, gas within vacuum system 36, and/or other components of system 10; parameters related to the respiration of subject 12; parameters related to a pressure support therapy regime; parameters related to an inexsufflation therapy regime; parameters related to suction therapy; and/or other parameters. For example, the one or more parameters may include one or more of a flow rate, a volume, a pressure, a composition (e.g., concentration(s) of one or more constituents), a temperature, a humidity, an acceleration, a velocity, and/or other parameters.

In some embodiments, sensor(s) 28 include a volume sensor, a flow rate sensor, a pressure sensor, and/or other sensors. Sensor(s) 28 may comprise one or more sensors that measure such parameters directly (e.g., through fluid communication with the flow of gas in flow manifold 14 and/or any other components of system 10). Sensor(s) 28 may comprise one or more sensors that generate output signals related to one or more parameters of the flow of gas indirectly. For example, one or more of sensor(s) 28 may generate an output based on an operating parameter of pressure support system 32 and/or mechanical inexsufflation system 34 (e.g., a valve driver or motor current, voltage, rotational velocity, and/or other operating parameters), and/or other information. Although sensor(s) 28 are illustrated at multiple specific locations within (or in communication with) system 10, this is not intended to be limiting. Sensor(s) 28 may include sensors disposed in a single location (e.g., within mechanical inexsufflation system 34 and/or pressure support system 32), in a plurality of locations different than those shown in FIG. 1, such as for example, within (or in communication with) interface appliance 62, and/or other locations. In some embodiments, sensor(s) may include a pneumotachometer located within mechanical inexsufflation system 34, a hot wire sensor, a cold wire sensor, a vortex sensor, a microelectromechanical systems (MEMS) device with and integrated heating element and temperature sensor, and/or other sensors.

Processor 30 is configured to provide information processing capabilities in system 10. As such, processor 30 may comprise one or more of a digital processor, an analog processor, a digital circuit designed to process information, an analog circuit designed to process information, a state machine, and/or other mechanisms for electronically processing information. Although processor 30 is shown in FIG. 1 as a single entity, this is for illustrative purposes only. In some implementations, processor 30 may comprise a plurality of processing units. These processing units may be physically located within the same device (e.g., pressure support system 32, mechanical inexsufflation system 34, vacuum system 36, etc.), or processor 30 may represent processing functionality of a plurality of devices operating in coordination. As shown in FIG. 1, processor 30 is operatively connected to pressure support system 32, mechanical inexsufflation system 34, vacuum system 36, valve 26, one or more sensors 28, user interface 50, and electronic storage 52. Processor 30 is configured by computer readable instructions and cooperable with the other components of system 10. Processor 30 may be configured to execute one or more computer program components and/or execute other programmed instructions. Processor 30 may be configured to execute components by software; hardware; firmware; some combination of software, hardware, and/or firmware; and/or other mechanisms for configuring processing capabilities on processor 30.

Processor 30 is configured to determine one or more parameters within system 10. The one or more parameters within system 10 may comprise gas parameters related to the flow of gas, breathing parameters of subject 12, parameters related to the pressure support therapy, parameters related to the inexsufflation therapy, parameters related to the suctioning therapy, and/or other parameters. Processor 30 is configured to determine the one or more parameters based on the output signals of sensors 28, and/or other information.

The information determined by processor 30 may be used for controlling pressure support system 32, mechanical inexsufflation system 34, vacuum system 36, valve 26, and/or other components of system 10; stored in electronic storage 52, displayed by user interface 50, and/or used for other purposes. By way of several non-limiting examples, the one or more gas parameters may include one or more of a volume, a pressure, a flow rate, a time, a humidity, a velocity, an acceleration, and/or other gas parameters of the flow gas determined based on output signals from one or more sensors 28. The breathing parameters may include, for example, an inspiratory capacity, a forced vital capacity, respiration rate, respiration (e.g., inhalation, exhalation, etc.) timing, and/or other parameters.

Processor 30 is configured to cause pressure support system 32, mechanical inexsufflation system 34, vacuum system 36, and/or other components of system 10 to deliver therapy to subject 12. Processor 30 is configured to cause pressure support system 32, mechanical inexsufflation system 34, vacuum system 36, and/or other components of system 10 to deliver therapy to subject 12 based on the information in the output signals from sensors 18, based on the determined parameters, based on information entered and/or selected by a user via user interface 50, and/or other information. As one example, processor 30 is configured to cause mechanical inexsufflation system 34 to deliver inexsufflation therapy by controlling mechanical inexsufflation system 34 to deliver a pressurized flow of breathable gas according to an inexsufflation therapy regime. Processor 30 is configured to control mechanical inexsufflation system 34 based on the output signals from sensors 28; gas, breathing, therapy, and/or other parameters determined by processor 30, information entered and/or selected by a user via user interface 50, and/or other information. This example applies similarly to pressure support system 32 and vacuum system 36.

In some embodiments, processor 30 is configured to control mechanical inexsufflation system 34 to provide the mechanical inexsufflation therapy to subject 12 such that a volume of gas exsufflated from the airway of subject 12 during an exsufflation phase of the mechanical inexsufflation therapy is equal to a volume of gas insufflated by subject 12 during a corresponding insufflation phase. Processor 30 is configured to control mechanical inexsufflation system 34 based on the information in the output signals from sensors 18, based on the parameters determined by processor 30, and/or based on other information. This equal volume M I-E mode ensures that subject 12's resting lung volume is maintained before and after an M I-E cycle. An excessive air removal from the lungs of subject 12 may cause atelectasis, lung de-recruitment, or loss of PEEP, for example. In some embodiments, processor 30 is configured such that a clinician may set (e.g., via user interface 50) a different target volume or set a different insufflation pressure and an insufflation time. Processor 30 is configured such that the exsufflation phase of an M I-E cycle removes the equal amount of volume delivered during the insufflation cycle.

In some embodiments, processor 30 is configured to determine a suctioning volume of gas suctioned by vacuum system 36, and, responsive to the suctioning volume of gas breaching a suctioning volume threshold, control valve 26 to change from operating in the second mode (facilitating mechanical inexsufflation and/or suctioning therapy) to operate in the first mode (facilitating pressure support therapy). In some embodiments, processor 30 is configured to determine the suctioning volume threshold based on a suctioning catheter diameter, an endotracheal tube diameter, and the volume of gas exsufflated from the airway of subject 12 during an exsufflation phase of the mechanical inexsufflation therapy.

The suctioning volume is drawn from two different pathways: the "upward" suctioning path and the "downward" suctioning path (e.g., as illustrated in FIG. 2). As described above, the terms "upward" and "downward" are not intended to be limiting and are used only to describe the relative relationship between the two pathways. The upward suctioning path is associated with the suction volume removed from the lung via an endotracheal tube (e.g., part of respiratory circuit 40) lumen without obstruction from a suction catheter (also shown and described in FIG. 2). The downward path is associated with the suction volume removed from a portion of the endotracheal tube where the suction catheter encroaches on the endotracheal tube lumen. The flow rate in both the downward and the upward pathways is governed by Poiseuille's Law, which describes that the mass flow rate is directly proportional to the applied pressure and the radius of the tube, and inversely proportional to the viscosity of air and the length of the tube. Processor 30 is configured to fix these parameters such that the flow rate is dictated by a difference in the radius of tubes (the endotracheal tube and the suction catheter) multiplied to the fourth power. According to Poiseuille's Law:

$$Q = \frac{\pi P r^4}{8 \eta l}$$

where Q is the flow rate, P is the pressure, r is the tube difference radius, n is the fluid viscosity, and l is the length of the tube.

In some embodiments, processor 30 is configured to determine the suctioning volume threshold based on entries or selections made by a user (e.g., a clinician) via user interface 50. In some embodiments, the suctioning volume threshold may be determined at manufacture of system 10. In some embodiments, the suctioning volume threshold may be determined based on the information in the output signals of sensors 18 during previous respiration of subject 12. For example, the suctioning volume threshold may be determined to be, or be determined based on, a previous tidal volume inhaled or exhaled by subject 12.

In some embodiments, processor 30 is configured such that the amount of the total suctioning volume is monitored indirectly by determining an amount of the volume removed via the "downward" (FIG. 2) suctioning path with a pneumotachometer (e.g., a sensor 18) built into mechanical inexsufflation system 34. (The volume removed from the "upward" direction is not measured because such a measurement would require an additional flow measurement device in the endotracheal tube (e.g., in respiratory circuit 40), which is not practical. The present system takes advantage of a built-in flow measurement system in M I-E system 34).

In some embodiments, processor 30 is configured to prompt a clinician (and/or other users) visually and/or audibly responsive to the total suctioning volume reaching a set target volume (e.g., or as a default, an immediately previously delivered tidal volume). In some embodiments, processor may control user interface 50 to prompt the clinician. In some embodiments, processor 30 may control vacuum system 36, mechanical inexsufflation system 34, and/or other components of system 10 to prompt the clinician. In some embodiments, the prompt comprises a displayed message, a tone, a flashing light, and/or other prompts. In some embodiments, responsive to being prompted, the clinician may manually adjust valve 26 to return valve 26 to the first mode of operation (e.g., to facilitate continued pressure support therapy), and/or take other actions.

By way of a non-limiting practical example, when suctioning therapy is indicated for subject 12, flow manifold 14 and valve 26 are configured such that a clinician may move valve 26 (e.g., a stopcock position that is part of valve 26) in flow manifold 14 to disconnect pressure support system 32 from respiratory circuit 40 and subject 12 and allow a mechanical inexsufflation and/or suctioning path to be connected to subject 12 (e.g., valve 26 may operate in the second mode to facilitate communication between ports 22, 20, and 18).

System 10 may be configured such that a clinician enters a desired hyperinflation volume/pressure via mechanical inexsufflation system 34, which may include at least a portion of user interface 50 (as described below), and a desired total volume/pressure for removal during the exsufflation phase of mechanical inexsufflation therapy. In some embodiments, system 10 may be configured to receive entry and/or selection (e.g., by a clinician) of an endotracheal tube (and/or other portion of respiratory circuit 40) size (e.g., diameter) and a suctioning catheter size (e.g., diameter), for example. Processor 30 may be configured to determine a total suctioning volume based on this information. For example, if the clinician enters an endotracheal tube size of 8 mm (e.g., an inside diameter of 8 mm) and a catheter size of 14 Fr (an inside diameter size of 4.7 mm), then processor 30 is configured such that the total suctioning volume is determined to be 3.3 (this is not intended to be limiting) times the "downward" (e.g., measures from mechanical inexsufflation system 34) suction volume. Otherwise, processor 30 may be configured such that a default value of 16 factor may be applied to the total suction volume determination.

Providing more detail for the example above, processor 30 may be configured such that, based on any entered and/or selected endotracheal tube (ETT) size and suction catheter (SC) size values, the following step by step operations may be performed and/or facilitated by processor 30 to determine a total suction volume:

1. Enter ETT size=X, SC size=Y
2. Convert SC French size (Y) to corresponding radius: r_sc=Y*0.165 [mm]
3. Determine radius of ETT: r_ett=X/2
4. Determine the corresponding cross-sectional area of SC: A_sc=pi*(r_sc)^2
5. Determine the corresponding cross-sectional area of ETT: A_ett=pi*(r_ett)^2
6. Determine the cross-sectional area of encroachment free area of ETT: A_ett_ef=A_ett−A_c
7. Determine the estimated radius of the encroachment free area of ETT: r_ett_ef=SQRT (A_ett_ef/pi)
8. Determine the ratio of radius between radius of the encroachment free of ETT and the radius of ETT: Ratio of radius=r_ett_ef/r_ett
9. Determine the upward flow rate factor=(Ratio of radius)^4
10. Determine the total suctioning volume=(1+upstream flow rate factor)* downward flow rate integrated over time For example, if a clinician enters an ETT of 8 and suction catheter size of 14 French as in the example above (with operations 1-10 below corresponding to operations 1-10 listed above:
1. ETT=8, SC=14
2. r_sc=14*0.165=2.3
3. r_ett=8/2=4
4. A_sc=pi*(2.3)^2=16.8
5. A_ett=pi*(4)^2=50.3
6. A_ett_ef=50.3−16.8=33.5
7. r_ett_ef=SQRT(33.5/pi)=3.3
8. Ratio of radius=4/3.3=1.2
9. Upward flow rate factor=1.2^4=2.3
10. Total suction volume=(1+2.3)*flow rate measured for M I-E integrated over time The example dimensions described above are not intended to be limiting. They are only examples. System 10 is configured to operate as described herein for a wide range of tube and catheter sizes.

Continuing with this practical example, system 10 may be configured such that a clinician may initiate mechanical inexsufflation (M I-E) augmented suctioning by delivering 3~4 (this example is not intended to be limiting) M I-E therapy. System 10 may be configured to facilitate advancement of a suctioning catheter (e.g., 202 shown in FIG. 2 and FIG. 3) through flow manifold 14 into an endotracheal tube that is part of respiratory circuit 40. System 10 may be configured such that a shorter version (e.g., relative to prior art systems) of catheter (e.g., a trach suctioning catheter) may be used (e.g., as selected by a clinician) to ensure that the tip of the suctioning catheter does not pass through the tip of the of the endotracheal tube and stimulate subject 12's carina. Once the suction catheter is inserted, system 10 may be configured such that the clinician may start the suctioning by pressing and holding a thumb (for example) port that is part of vacuum system 36 (e.g., as described herein). Mechanical inexsufflation system 34, processor 30 (via the information in output signals from sensors1 18), and/or other components of system 10 may continuously measure and monitor a total suctioning volume. Processor 30 may prompt the clinician by way of a visual and/or audible alarm (e.g., presented via user interface 50 as described below) responsive to the total suctioning volume reaching the target set volume. System 10 (processor 30) may be configured such that a default total suctioning volume is a last delivered tidal volume, for example. In some embodiments, processor 30 and vacuum system 36 may be configured such that suctioning therapy may be automatically stopped by means of an electric, pneumatic, mechanical, and/or other control signals based on the information in the output signals from sensors 18, the total suctioning volume, the volume threshold, and/or other information.

In some embodiments, valve 26 may be configured such that, once the M I-E augmented suctioning is completed, the clinician may move valve 26 (e.g., turn a stopcock of valve 26) to the pressure support therapy position (e.g., to the first mode of operation) to close the suctioning path and resume the pressure support therapy. In some embodiments, valve 26 may be configured such that, once the M I-E augmented suctioning is completed, valve 26 is controlled by processor 30 to return to the pressure support therapy position (e.g., to the first mode of operation) to close the suctioning path and resume the pressure support therapy.

User interface 50 is configured to provide an interface between system 10 and subject 12 and/or other users through which subject 12 and/or other users may provide information to and receive information from system 10. Other users may comprise a caregiver, a doctor, a decision maker, and/or other users. This enables data, cues, results, and/or instructions and any other communicable items, collectively referred to as "information," to be communicated between a user (e.g., subject 12) and one or more of valve 26, pressure support system 32, mechanical inexsufflation system 34, vacuum system 36, processor 30, electronic storage 52, and/or other components of system 10. Examples of interface devices suitable for inclusion in user interface 50 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 50 comprises two or more separate interfaces (e.g., individual interfaces associated with flow manifold 14 and/or valve 26, pressure support system 32, mechanical inexsufflation system 34, vacuum system 36, etc.). In one embodiment, user interface 50 comprises at least three separate interfaces that are provided integrally with pressure support system 32, mechanical inexsufflation system 34, and vacuum system 36.

It is to be understood that other communication techniques, either hard-wired or wireless, are also contemplated by the present disclosure as user interface 50. For example, the present disclosure contemplates that user interface 50 may be integrated with a removable storage interface provided by electronic storage 52. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 50 comprise, but are not limited to, an RS-232 port, RF link, an IR link, modem (telephone, cable, or other), a link to cloud storage, etc. In short, any technique for communicating information with system 10 is contemplated by the present disclosure as user interface 50.

Electronic storage 52 comprises electronic storage media that electronically stores information. The electronic storage media of electronic storage 52 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 52 may comprise one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 52 may store software algorithms, information determined by processor 30, information received via user interface 50, and/or other information that enables system 10 to function properly. Electronic storage 52 may be (in whole or in part) a separate component within system 10, or electronic storage 52 may be provided (in whole or in part) integrally with one or more other components of system 10 (e.g., user interface 50, processor 30, vacuum system 36, mechanical inexsufflation system 34, pressure support system 32, etc.).

Figure 4:
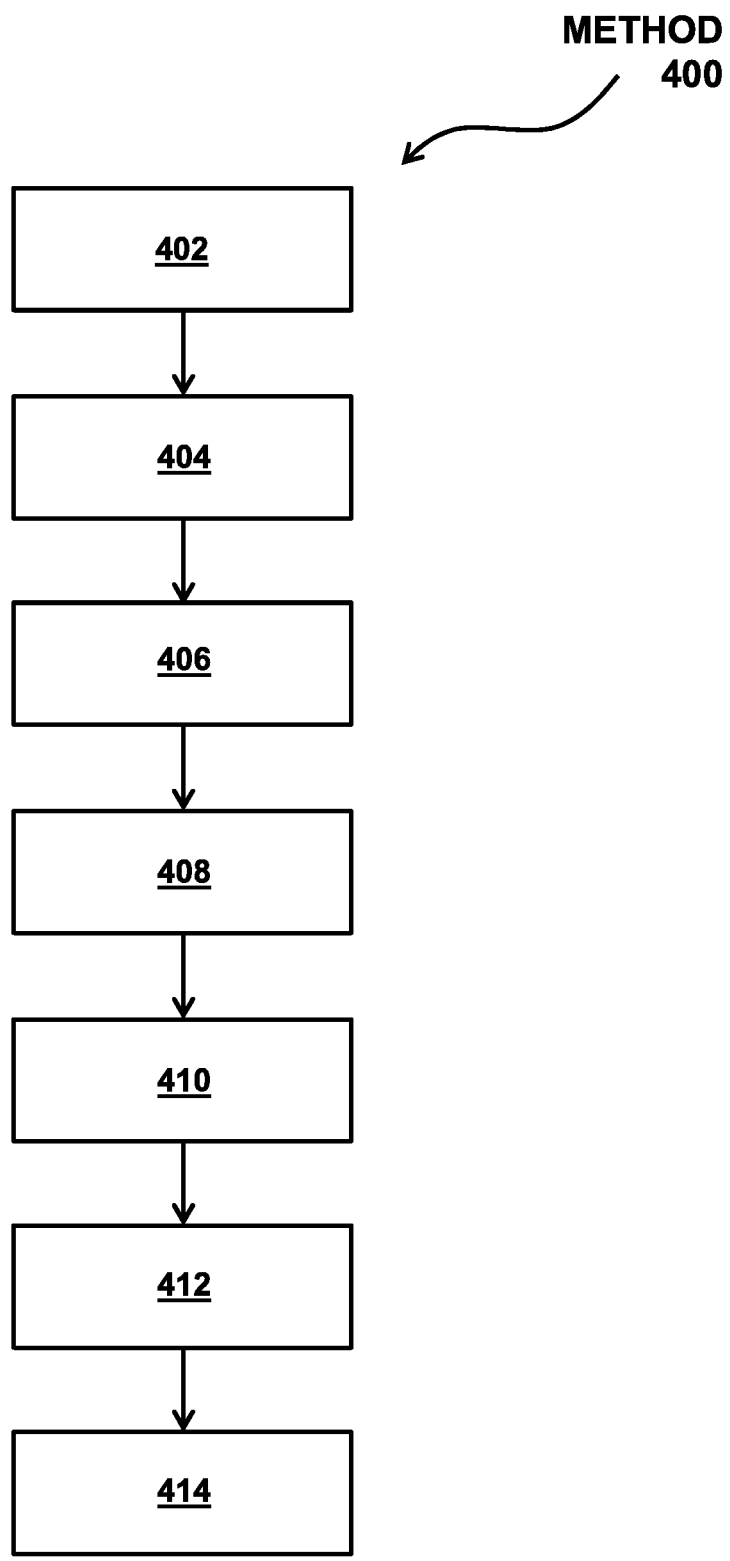
FIG. 4 illustrates a method for facilitating pressure support therapy, mechanical inexsufflation therapy, and suctioning therapy for a subject with a therapy system.

FIG. 4 illustrates a method 400 for facilitating pressure support therapy, mechanical inexsufflation therapy, and suctioning therapy for a subject with a therapy system. In some embodiments, the system comprises a flow manifold, a valve, and/or other components. In some embodiments, the system comprises the flow manifold, the valve, one or more sensors, one or more processors, a pressure support system, an inexsufflation system, a vacuum system, and/or other components. The operations of method 400 presented below are intended to be illustrative. In some embodiments, method 400 may be accomplished with one or more additional operations not described, and/or without one or more of the operations discussed. Additionally, the order in which the operations of method 400 are illustrated in FIG. 4 and described below is not intended to be limiting.

In some embodiments, one or more portions of method 400 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 400 in response to instructions stored electronically on an electronic storage medium. The one or more processing devices may include one or more devices configured through hardware, firmware, and/or software to be specifically designed for execution of one or more of the operations of method 400.

At an operation 402, communication between the pressure support system, the mechanical inexsufflation system, the vacuum system, and the respiratory circuit is facilitated. The respiratory circuit is in communication with an airway of the subject. In some embodiments, operation 402 is performed by a flow manifold the same as or similar to flow manifold 14 (shown in FIG. 1 and described herein).

The flow manifold comprises a plurality of ports configured to removably couple with the pressure support system, the mechanical inexsufflation system, the vacuum system, and the respiratory circuit. The flow manifold comprises a flow channel configured to place the respiratory circuit in fluid communication with the pressure support system, the mechanical inexsufflation system, and the vacuum system by connecting the plurality of ports to each other.

At an operation 404, gas flow between the respiratory circuit and the pressure support system is facilitated to provide the pressure support therapy to the subject. The gas flow between the respiratory circuit and the pressure support system is facilitated by the valve operating in a first mode. In some embodiments, operation 404 is performed by a valve the same as or similar to valve 26 (shown in FIG. 1 and described herein).

At operation 406, gas flow between the respiratory circuit, the mechanical inexsufflation system, and the vacuum system is facilitated to provide the mechanical inexsufflation therapy and the suctioning therapy to the subject. The gas flow between the respiratory circuit, the mechanical inexsufflation system, and the vacuum system is facilitated by the valve operating in a second mode. In some embodiments, the flow channel is closed to ambient atmosphere when the valve operates in the first mode and the second mode. In some embodiments, operation 406 is performed by a valve the same as or similar to valve 26 (shown in FIG. 1 and described herein).

At operation 408, output signals conveying information related to gas flow through the flow manifold are generated. In some embodiments, operation 408 is performed by one or more sensors the same as or similar to one or more sensors 28 (shown in FIG. 1 and described herein).

At operation 410, the pressure support system is controlled to provide the pressure support therapy to the subject based on the information in the output signals. In some embodiments, operation 410 is performed by a processor the same as or similar to processor 30 (shown in FIG. 1 and described herein).

At operation 412, the mechanical inexsufflation system is controlled, based on the output signals, to provide the mechanical inexsufflation therapy to the subject such that a volume of gas exsufflated from the airway of the subject during an exsufflation phase of the mechanical inexsufflation therapy is equal to a volume of gas insufflated by the subject during a corresponding insufflation phase. In some embodiments, operation 412 is performed by a processor the same as or similar to processor 30 (shown in FIG. 1 and described herein).

At operation 414, a suctioning volume of gas suctioned by the vacuum system is determined, and, responsive to the suctioning volume of gas breaching a suctioning volume threshold, the valve is controlled to change from operating in the second mode to operate in the first mode. In some embodiments, the suctioning volume threshold is determined based on a suctioning catheter diameter, an endotracheal tube diameter, and the volume of gas exsufflated from the airway of the subject during the exsufflation phase of the mechanical inexsufflation therapy. In some embodiments, operation 414 is performed by a processor the same as or similar to processor 30 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to facilitate pressure support therapy, mechanical inexsufflation therapy, and suctioning therapy for a subject, the system comprising:
 a flow manifold configured to communicate with a pressure support system, a mechanical inexsufflation system, a vacuum system, and a respiratory circuit, the respiratory circuit in communication with an airway of the subject, the flow manifold comprising:
 a plurality of ports configured to removably couple with the pressure support system, the mechanical inexsufflation system, the vacuum system, and the respiratory circuit;
 and
 a flow channel configured to place the respiratory circuit in fluid communication with the pressure support system, the mechanical inexsufflation system, and the vacuum system by connecting the plurality of ports to each other; and a valve positioned to coordinate fluid coupling of the plurality of ports to the flow channel;

the valve being configured to be positioned in a first mode wherein ports of the respiratory circuit and the pressure support system are coupled to the flow channel to facilitate gas flow between the respiratory circuit and the pressure support system to provide the pressure support therapy to the subject, wherein a port of the vacuum system and a port of the mechanical inexsufflation system i- are decoupled from the flow channel in the first mode; and the valve configured to be repositioned in a second mode wherein the pressure support system is decoupled from the respiratory circuit, and the mechanical inexsufflation system and the vacuum system are both coupled to the flow channel to facilitate gas flow between the respiratory circuit, the mechanical inexsufflation system, and the vacuum system to provide the mechanical inexsufflation therapy and the suctioning therapy to the subject simultaneously.

2. The system of claim 1, wherein the flow channel is closed to ambient atmosphere when the valve operates in the first mode and the second mode.

3. The system of claim 1, wherein the plurality of ports comprises:
a first port configured to couple with the pressure support system;
a second port configured to couple with the mechanical inexsufflation system;
a third port configured to couple with the vacuum system; and
a fourth port configured to couple with the respiratory circuit, and wherein the valve is configured to facilitate gas flow between the fourth port and the first port in the first mode; and facilitate gas flow between the fourth port, the third port, and the second port in the second mode.

4. The system of claim 3, wherein the third port is configured to receive a suctioning catheter of the vacuum system, and wherein the third port, the valve, and the flow channel are configured to facilitate advancement of the suctioning catheter through the flow channel and the fourth port into an endotracheal tube of the respiratory circuit.

5. The system of claim 1, further comprising one or more sensors configured to generate output signals conveying information related to gas flow through the flow manifold; and
one or more processors in operative communication with the one or more sensors, the pressure support system, the mechanical inexsufflation system, and/or the vacuum system, the one or more processors configured by computer readable instructions to:
control the pressure support system to provide the pressure support therapy to the subject based on the information in the output signals;
control, based on the information in the output signals, the mechanical inexsufflation system to provide the mechanical inexsufflation therapy to the subject such that a volume of gas exsufflated from the airway of the subject during an exsufflation phase of the mechanical inexsufflation therapy is equal to a volume of gas insufflated by the subject during a corresponding insufflation phase; and/or determine, based on the information in the output signals, a suctioning volume of gas suctioned by the vacuum system, and, responsive to the suctioning volume of gas breaching a suctioning volume threshold, controlling the valve to change from operating in the second mode to operate in the first mode.

6. The system of claim 5, further comprising the pressure support system, the inexsufflation system, and the vacuum system.

7. The system of claim 5, wherein the one or more sensors comprise a pneumotachometer.

8. The system of claim 5, wherein the one or more processors are configured to determine the suctioning volume threshold based on a suctioning catheter diameter, an endotracheal tube diameter, and the volume of gas exsufflated from the airway of the subject during the exsufflation phase of the mechanical inexsufflation therapy.

9. The system of claim 1, wherein the valve is configured to be manually changed between operating in the first mode and operating in the second mode.

10. The system of claim 1, wherein the flow manifold comprises a housing configured to hold the flow channel and the valve.

11. A method for facilitating pressure support therapy, mechanical inexsufflation therapy, and suctioning therapy for a subject with a therapy system, the system comprising a flow manifold and a valve, the method comprising:
facilitating, with positioning of a valve of the flow manifold, communication between a pressure support system, a mechanical inexsufflation system, a vacuum system, and a respiratory circuit, the respiratory circuit in communication with an airway of the subject, the flow manifold comprising:
a plurality of ports configured to removably couple with the pressure support system, the mechanical inexsufflation system, the vacuum system, and the respiratory circuit; and
a flow channel configured to place the respiratory circuit in fluid communication with the pressure support system, the mechanical inexsufflation system, and the vacuum system by connecting the plurality of ports to each other;
coordinating, using the valve, fluid coupling of the plurality of ports to the flow channel;
facilitating, with positioning of the valve to operate in a first mode wherein ports of the respiratory circuit and the pressure support system are coupled to the flow channel, gas flow between the respiratory circuit and the pressure support system to provide the pressure support therapy to the subject, wherein a port of the vacuum system and a port of the mechanical inexsufflation system are not coupled to the flow channel in the first mode; and
facilitating, with repositioning of the valve to operate in a second mode wherein the pressure support system is decoupled from the respiratory circuit and the mechanical inexsufflation system and the vacuum system are both coupled to the flow channel, gas flow between the respiratory circuit, the mechanical inexsufflation system, and the vacuum system to provide the mechanical inexsufflation therapy and the suctioning therapy to the subject simultaneously.

12. The method of claim 11, wherein the flow channel is closed to ambient atmosphere when the valve operates in the first mode and the second mode.

13. The method of claim 11, further comprising generating, with one or more sensors of the system, output signals conveying information related to gas flow through the flow manifold;
  controlling, with one or more processors of the system, the pressure support system to provide the pressure support therapy to the subject based on the information in the output signals;
  controlling, with the one or more processors, based on the information in the output signals, the mechanical inexsufflation system to provide the mechanical inexsufflation therapy to the subject such that a volume of gas exsufflated from the airway of the subject during an exsufflation phase of the mechanical inexsufflation therapy is equal to a volume of gas insufflated by the subject during a corresponding insufflation phase; and/or
  determining, with the one or more processors, based on the information in the output signals, a suctioning volume of gas suctioned by the vacuum system, and, responsive to the suctioning volume of gas breaching a suctioning volume threshold, controlling the valve to change from operating in the second mode to operate in the first mode.

14. The method of claim 13, further comprising determining, with the one or more processors, the suctioning volume threshold based on a suctioning catheter diameter, an endotracheal tube diameter, and the volume of gas exsufflated from the airway of the subject during the exsufflation phase of the mechanical inexsufflation therapy.

15. A method comprising:
  coordinating, using a valve positioned in a flow manifold, fluid coupling of a plurality of ports to a flow channel of a respiratory circuit
  positioning the valve in a first mode to provide gas flow between a pressure support system and the flow channel of the respiratory circuit leading to a patient via a pressure support system port;
  repositioning the valve in a second mode to close the pressure support system port and open both of a mechanical inexsufflation port and a vacuuming port and to allow advancement of a vacuum system into the flow channel of the respiratory circuit and past the pressure support system port to provide mechanical inexsufflation and suctioning to the subject simultaneously;
  thereafter providing one or more of mechanical inexsufflation and vacuuming of the the flow channel of the respiratory circuit; and
  returning the valve to the first position to provide gas flow between the pressure support system and the flow channel of the respiratory circuit and to disconnect the vacuuming port and mechanical inexsufflation port by operation of the valve.

16. The method of claim 15, wherein one or more of the positioning, the repositioning and the returning comprises rotating a stopcock of the valve.

17. The method of claim 15, wherein a single movement of the valve disconnects both of the vacuuming port and the mechanical inexsufflation port.

18. The method of claim 15, wherein the vacuuming port and the mechanical inexsufflation port share a common passage to the valve.

19. The method of claim 18, comprising advancement of the vacuum system into the flow channel and past the pressure support system port comprises advancing the vacuum system through the valve.

* * * * *